(12) United States Patent
Cheng

(10) Patent No.: US 10,717,665 B2
(45) Date of Patent: Jul. 21, 2020

(54) MULTI-STAGE MEDICAL SEWAGE STERILIZATION DEVICE AND METHOD BASED ON GRAPHENE NANO TECHNOLOGIES

(71) Applicant: SHAOGUAN UNIVERSITY, Shaoguan, Guangdong (CN)

(72) Inventor: Jinsheng Cheng, Guangdong (CN)

(73) Assignee: SHAOGUAN UNIVERSITY, Shaoguan (CN)

( * ) Notice: Subject to any disclaimer, the term of this patent is extended or adjusted under 35 U.S.C. 154(b) by 86 days.

(21) Appl. No.: 16/177,414

(22) Filed: Oct. 31, 2018

(65) Prior Publication Data

US 2019/0382296 A1 Dec. 19, 2019

(30) Foreign Application Priority Data

Jun. 14, 2018 (CN) .......................... 2018 1 0612743
Jun. 14, 2018 (CN) .......................... 2018 1 0613329

(51) Int. Cl.
  *C02F 9/02* (2006.01)
  *C02F 9/12* (2006.01)
  (Continued)

(52) U.S. Cl.
  CPC ................ *C02F 9/00* (2013.01); *A61L 2/022* (2013.01); *A61L 2/025* (2013.01); *A61L 2/085* (2013.01);
  (Continued)

(58) Field of Classification Search
  CPC .... C02F 1/001; C02F 1/30; C02F 1/32; C02F 1/36; C02F 1/50; C02F 1/725; C02F 9/00; C02F 9/005; C02F 2001/007; C02F 2103/003; C02F 2301/08; C02F 2303/04; C02F 2303/24; C02F 2305/08; C02F 2305/10; A61L 2/022; A61L 2/025; A61L 2/085; A61L 2/088; A61L 2/26;
  (Continued)

(56) References Cited

U.S. PATENT DOCUMENTS

| 4,042,509 A | * | 8/1977 | Bowen | ...................... | C02F 9/00 |
| | | | | | 210/192 |
| 2009/0145855 A1 | * | 6/2009 | Day | ...................... | C02F 1/325 |
| | | | | | 210/748.11 |
| 2019/0070533 A1 | * | 3/2019 | Cheng | ...................... | B01D 29/56 |

FOREIGN PATENT DOCUMENTS

| CN | 103214133 B | 1/2015 |
| CN | 104150698 B | 4/2016 |
| CN | 106957079 A | 7/2017 |

* cited by examiner

*Primary Examiner* — Matthew O Savage
(74) *Attorney, Agent, or Firm* — Wayne & Ken, LLC; Tony Horn

(57) ABSTRACT

The invention relates to a multi-stage medical sewage sterilization device and method based on graphene nano technologies. The multi-stage sterilization device comprises multiple stages of graphene nano composite sterilization grids, a graphene photocatalytic sterilization tank, a graphene-modified diatom ceramic disinfection tank, an ultrasonic sterilization tank and a laser and near-infrared sterilization device. Compared with a traditional method, the present invention has a more thorough killing or blocking effects on pathogenic bacteria, parasite eggs and the like in various medical sewages. In addition, the device of the present invention can be disassembled and cleaned regularly, and has a long service life, thus the process cost is reduced.

10 Claims, 1 Drawing Sheet

(51) Int. Cl.
*C02F 9/00* (2006.01)
*A61L 2/02* (2006.01)
*A61L 2/025* (2006.01)
*A61L 2/08* (2006.01)
*A61L 2/26* (2006.01)
*B01J 21/06* (2006.01)
*B01J 21/18* (2006.01)
*B01J 35/00* (2006.01)
*B01J 35/04* (2006.01)
*B01D 39/20* (2006.01)
*C02F 1/30* (2006.01)
*C02F 1/72* (2006.01)
*B82Y 30/00* (2011.01)
*C02F 103/00* (2006.01)
*C02F 1/00* (2006.01)
*C02F 1/36* (2006.01)
*C02F 1/32* (2006.01)

(52) U.S. Cl.
CPC ............... *A61L 2/088* (2013.01); *A61L 2/26* (2013.01); *B01D 39/2055* (2013.01); *B01J 21/063* (2013.01); *B01J 21/18* (2013.01); *B01J 35/004* (2013.01); *B01J 35/0013* (2013.01); *B01J 35/04* (2013.01); *C02F 1/30* (2013.01); *A61L 2202/11* (2013.01); *B82Y 30/00* (2013.01); *C02F 1/001* (2013.01); *C02F 1/32* (2013.01); *C02F 1/36* (2013.01); *C02F 1/725* (2013.01); *C02F 2103/003* (2013.01); *C02F 2303/04* (2013.01); *C02F 2305/08* (2013.01); *C02F 2305/10* (2013.01)

(58) Field of Classification Search
CPC ...... A61L 2202/11; B01J 21/063; B01J 21/18; B01J 35/0031; B01J 35/004; B01J 35/04; B82Y 30/00; B01D 29/0018; B01D 29/002; B01D 29/56; B01D 35/16; B01D 39/2055
See application file for complete search history.

U.S. Patent              Jul. 21, 2020           US 10,717,665 B2
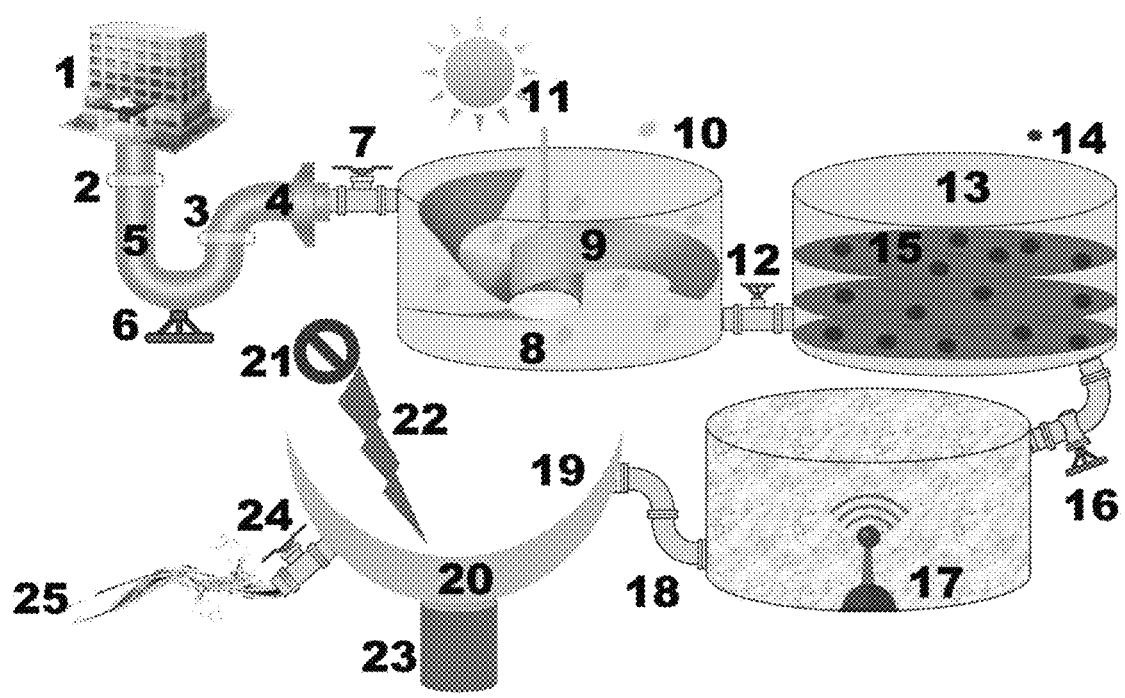

MULTI-STAGE MEDICAL SEWAGE STERILIZATION DEVICE AND METHOD BASED ON GRAPHENE NANO TECHNOLOGIES

CROSS-REFERENCE TO RELATED APPLICATIONS

This application claims the benefit of priority from Chinese Application No. 201810612743.2 and 201810613329.3, filed on Jun. 14, 2018. The content of the aforementioned applications, including any intervening amendments thereto, are incorporated herein by reference.

TECHNICAL FIELD

The invention relates to the technical field of medical sewage sterilization, in particular to a multi-stage medical sewage sterilization device and method based on graphene nano technologies.

BACKGROUND OF THE PRESENT INVENTION

Medical sewage mainly refers to sewage discharged from different hospital units such as outpatient treatment room, testing laboratory, ward (including laminar-flow clean ward), laundry room, dressing change room, injection room, ICU room, X-ray room, burn ward, operating room (including laminar-flow clean operating room), blood bank, experiment laboratory, infectious disease treatment area, protective isolation ward, sterile supply room, hospital toilet or laundry room. The sources and components of the sewage are very complex, and the sewage contains a large number of pathogenic bacteria, viruses and chemical agents, such as drugs, disinfectants, diagnostic agents, detergents, as well as a large number of pathogenic microorganisms, parasite eggs and various viruses, such as ascaris eggs, hepatitis virus, tubercle bacillus and dysentery bacteria, thus having the characteristics of space pollution, acute infection and latent infection (Qu Jijun, He Zheng, Lin Yaokun. Investigation on Sterilization of Medical Sewage in Some Hospitals in Guangzhou [J]. Chinese Journal of Public Health Management, 2010, 26 (3): 298-299). In particular, bacteria, viruses and parasite eggs in hospital sewage have certain resistance in the environment, some of which live in sewage for a long time. When people eat or come into contact with water or vegetables contaminated by bacteria, viruses, parasite eggs and toxic and harmful substances, they will cause diseases or cause outbreaks of infectious diseases. Through epidemiological investigation and bacteriological examination, it has been proved that all previous outbreaks of large-scale infectious diseases in China are related to drinking or contacting contaminated water. For example, a large-scale outbreak of hepatitis A occurred in Shanghai in 1988, which was caused by contamination of clams by dung boats carrying hepatitis A virus (Ye Wanfang, Cai Tongzhang. CLINICAL COURSE AND PROGNOSIS OF VIRAL HEPATITIS IN A 1988 SHANGHAI EPIDEMIC—A FIVE YEARS FOLLOW-UP STUDY OF 1075 CASES . . . [J]. Shanghai Medical Science, 1993, 16 (11): 629-632) In recent years, *cholera* has occurred in many countries in the world, with a wide outbreak area and a large number of deaths, which is rare in history, and most of the cases have occurred in coastal areas of underdeveloped countries. It is reported that all these cases are due to the fact that the drinking water is contaminated by excrement of patients.

Compared with industrial waste water and domestic waste water, the medical sewage has the characteristics of small amount and strong pollution. If the medical sewage is allowed to be discharged, it will seriously pollute water sources and spread diseases.

According to the data of the International Bureau of Statistics of China in 2009, the national discharge of medical sewage was 446.548 million tons, but the qualified discharge was only 388.602 million tons, with a compliance rate of 87.0%. The discharge of COD in medical sewage amounted to 702.749 million tons, and the discharge of ammonia nitrogen amounted to 73.528 million tons. Data of Guangdong Province in the same year showed that the medical sewage discharge was 45.595 million tons, but the qualified discharge was only 37.039 million tons, with a compliance rate of only 81.23%, which is significantly lower than the national average compliance rate. The alarming data warns that the safety and qualified discharge of medical sewage in Guangdong province and even the whole country still has a long way to go. Because it is related to life safety, environmental safety or public health, China is cautious about medical sewage discharge and increasingly strict in management, which also puts forward higher requirements for medical sewage sterilization technology.

The existing medical sewage treatment technologies are of varying quality. Some enterprises have only made some improvements on the traditional industrial sewage treatment technology by adding sterilization procedures, such as adding ultraviolet disinfection, hydrogen peroxide or ozone disinfection technology, etc. (Li Jian. Study on Disinfection treatment and Practical Application of Hospital wastewater containing bacteria [D]. Jilin University, 2011). Some organizations have explored the medical sewage sterilization process of "hydrolytic acidification+biological contact oxidation+disinfection" (Liu Xi. Hospital Wastewater Treatment with the Hydrolysis Oxidization Technology [J]. Journal of Environment and Health, 2005, 22 (3): 209-211). There are also researchers who have come up with such a design that a closed water collection tank, a closed primary sedimentation tank, a closed sludge tank, a closed sludge disinfection tank, a closed sewage sterilization tank, a coagulation tank, a coagulation sedimentation tank, a biological filter tower and a secondary sedimentation tank which are connected in sequence for medical sewage treatment (Dong Yubo. Medical Wastewater Purification Recovery Treatment System Mainly Based on Flocculation and Biologic Filter. ZL 101591096). Xu Weiqi et al., have developed a treatment agent for medical sewage, including titanium dioxide 20-200, silicon dioxide 40-300, zinc acetate 40-120, etc., and used it in disinfection and evaporation of medical sewage (Xu Weiqi. Treatment Agent for Medical Sewage and Method for Odorless Treatment of Medical Sewage. ZL 201711088979.2). Shao Chunyan et al., have developed a self-control disinfection device for medical wastewater, which is characterized in that a water injection opening is formed in the top of an upper-layer medicine dissolving box and a medicine feeding opening is formed in the upper part of the medicine dissolving box; an emptying opening is formed in the lower part of the medicine dissolving box and a stirring pump is mounted in the medicine dissolving box; an electric control part of disinfection equipment and a medicine feeding pump are mounted in an electric control cabinet; a medicine suction pipe of the medicine feeding pump is communicated with the medicine dissolving box; a medicine discharging pipe of the medicine feeding pump is communicated with a disinfection box; a high-liquid-level automatic valve is arranged at the upper part of the medicine dissolving box; a low-liquid-level automatic valve is arranged at the lower part of the medicine dissolving box; a sewage water inlet and a processed-water water outlet are formed in the upper part of a lower-layer disinfection box; an emptying opening is formed in the bottom of the disinfection box. (Shao Chunyan, Chen Shourong, Wu Di, Wang Hongning, Jiang Haichang. Self-control Disinfection Device for Medical Wastewater. ZL 201711161454.7).

However, it is worth noting that the existing traditional medical sewage sterilization process still faces the problem of incomplete sterilization, for example, some pathogenic bacteria, including common bacteria, viruses, spirochetes, rickettsia, chlamydia, mycoplasma, fungi and actinomycetes still remain (Lu Xuekui, Hua Yijiang, Jia Qiufang. Investigation on Disinfection Effect of Medical Sewage [J]. Chinese Journal of Disinfection, 2007, 24 (1): 88-88). If the medical sewage that is not thoroughly treated and fails to meet the standard is still discharged to the outside, it will easily cause public health incidents and the social impact will be unprecedented. The market also calls for a new medical sewage sterilization technology and related devices that are thorough and efficient in medical sewage sterilization and simple and inexpensive.

SUMMARY OF THE PRESENT INVENTION

In view of the forgoing, it is therefore an object of the present invention to provide a multi-stage medical sewage sterilization device and method based on graphene nano technologies, which can improve the safety of medical sewage discharge.

The object of the present invention is achieved by the following technical scheme: a multi-stage medical sewage sterilization device based on graphene nano technologies, including:

a sewage discharge unit including sequentially a first-stage graphene nano composite grid, a second-stage graphene nano composite grid and a third-stage graphene nano composite grid along a water flow direction, wherein mesh numbers of the first, second and third-stage graphene nano composite grids are sequentially increased;

a sterilization unit connected with the sewage discharge unit through a first-stage water valve, and medical sewage sequentially passes through the three stages of graphene nano composite grids and enters the sterilization unit; the sterilization unit sequentially includes a graphene photocatalytic sterilization tank, a graphene-modified diatom ceramic disinfection tank, an ultrasonic sterilization tank and a laser sterilization device along a water flow direction, and adjacent components are connected through a second-stage water valve, a third-stage water valve and a fourth-stage water valve; a wall of the graphene photocatalytic sterilization tank is made of transparent material, an inner wall of the graphene photocatalytic sterilization tank is provided with a graphene nano composite coating, and the interior of the graphene photocatalytic sterilization tank is filled with graphene photocatalytic sterilization agent; the graphene-modified diatom ceramic disinfection tank is internally provided with multiple layers of graphene-reinforced polymer screens each having a graphene-modified diatom ceramic composite material provided thereon; and the laser sterilization device includes a laser condensing cavity and a laser generator, a laser beam generated by the laser generator enters the laser condensing cavity, and a graphene near-infrared nano coating is provided on an inner wall of the laser condensing cavity.

Compared with the prior art, the device of the invention has a more thorough killing or blocking effect on pathogenic bacteria, parasite eggs and the like in various medical sewages, and the detection indexes of the medical sewage after the final sterilization treatment are as follows: three consecutive samples of 500 ml sewage are taken for detection after sterilization, and no pathogenic bacteria or parasite eggs shall be detected; the total number of coliform bacteria per liter shall not be more than 100 and shall conform to relevant national standards. In addition, the device of the present invention can be disassembled and cleaned regularly, and has a long service life, thus the process cost is reduced.

Further, the first-stage graphene nano composite grid has a mesh number of 50-120; the second-stage graphene nano composite grid has a mesh number of 120-250; and the third-stage graphene nano composite grid has a mesh number of 270-600. The first two stages of graphene nano composite grids can filter and remove sand, rust, fine sediment, flocculent floaters and the like in the medical sewage stage by stage, and the third-stage graphene nano composite grid can further block residual solid contaminants. The three stages of graphene nano composite grids are adjustable in mesh number and can be regularly disassembled and cleaned to remove residual contaminants.

Furthermore, a U-shaped graphene-reinforced polymer sewage discharge pipe is arranged between the first-stage graphene nano composite grid and the second-stage graphene nano composite grid, which is provided at the bottom thereof with a solid contaminant separation valve. Residual solid contaminants slowly settling in the medical sewage passing through the first-stage graphene nano composite grid are discharged through the solid contaminant separation valve, and solid contaminants not passing through the second-stage graphene nano composite grid also settle down and are discharged through the solid contaminant separation valve.

Further, the graphene-modified diatom ceramic composite material is wrapped with a 100-325 mesh recycled fiber cloth or glass fiber cloth.

Further, the graphene-modified diatom ceramic composite material is formed by mixing a graphene oxide/superparamagnetic nanoparticle composite material and a graphene-reinforced diatom ceramic material in a mass ratio of 20:80 to 30:70.

Further, in the graphene oxide/superparamagnetic nanoparticle composite material, the graphene oxide accounts for 2.5-25%, and the superparamagnetic nanoparticles have a particle size of less than 10 nm. The material of the superparamagnetic nanoparticles may be any one or more of $\gamma$-$Fe_2O_3$, $Fe_3O_4$ and $Y_2O_3$. Both the graphene oxide and the superparamagnetic material with a particle size of less than 10 nm have excellent antibacterial activity. After forming the composite material, a superimposed sterilization effect will be produced and possible pathogenic bacteria present in water such as *Escherichia coli, cholera* bacteria, *Shigella dysenteriae, salmonella, Klebsiella, schistosoma* pathogen, etc., can be better killed, thus achieving a further purification effect.

Further, the graphene-reinforced diatom ceramic material is prepared by sintering the following components in percentage by weight: 30-50% of diatomite, 10-30% of kaolin, 7-15% of feldspar, 2-15% of graphene, 2-4% of alumina, 2-4% of boron glass, 2-3% of talcum powder and 3-5% of quartz powder. A composite of the graphene oxide/superparamagnetic nanoparticle composite material and the graphene-reinforced diatom ceramic material can form a certain "microchannel network" to effectively isolate or kill pathogenic bacteria with larger size.

Further, the ultrasonic power in the ultrasonic sterilization tank is 100 W to 500 KW, and the sterilization is performed for 10 to 60 min. Ultrasonic sterilization is an effective auxiliary sterilization method, which has the advantages of low energy consumption and short sterilization time.

Further, the bottom of the laser condensing cavity is fixed on a rotatable sterilization tank base which rotates at a speed of 5-60 rpm. Through rotation of the base, near-infrared light can be absorbed at all angles in the condensing cavity, and residual bacteria can be quickly killed by heating up. Combined with the sterilization effect of the laser beam itself, the sterilization of medical sewage can be more uniform and thorough.

The present invention also provides a multi-stage medical sewage sterilization method based on graphene nano technologies, by which the medical sewage is sequentially passed through three stages of graphene nano composite grids with an increasing mesh number to obtain a preliminary sterilized water body; and then the preliminary sterilized water body is sequentially subjected to graphene photocatalytic sterilization, graphene-modified diatom ceramic composite sterilization, ultrasonic sterilization, laser and near-infrared sterilization to obtain a final sterilized water body.

For a better understanding and implementation, the present invention will be described in detail below with reference to the accompanying drawings.

BRIEF DESCRIPTION OF THE DRAWINGS

FIG. 1 is a schematic diagram of a multi-stage medical sewage sterilization device based on graphene nano technologies of the present invention.

DESCRIPTION OF REFERENCE NUMBERS IN THE DRAWINGS

1. Medical institution unit; 2. First-stage graphene nano composite grid; 3. Second-stage graphene nano composite grid; 4. Third-stage graphene nano composite grid; 5. U-shaped graphene-reinforced polymer sewage discharge pipe; 6. Solid contaminant separation valve; 7: First-stage water valve; 8. Graphene photocatalytic sterilization tank; 9. Stirring device; 10. Graphene photocatalytic sterilization agent; 11. Power control device; 12: Second-stage water valve; 13. Graphene-modified diatom ceramic disinfection tank; 14. Graphene-modified diatom ceramic composite material; 15. Graphene-reinforced polymer screen; 16: Third-stage water valve; 17: Ultrasonic sterilization tank; 18: Fourth-stage water valve; 19: Graphene near-infrared nano coating; 20: Laser condensing cavity; 21: Laser generator; 22: Laser beam; 23: rotatable sterilization tank base; 24: Fifth-stage water valve; 25: Sterilized water.

DETAILED DESCRIPTION OF THE PRESENT INVENTION

In light of the current status of medical water sterilization and the requirements on sterilization technologies, and by fully utilizing the characteristics of graphene such as super-large specific surface, good photocatalytic degradation performance, excellent near-infrared thermal effect, functional modification, and excellent bacteria inactivation or blocking characteristics, the invention provides a multi-stage sterilization device and method for various medical sewages such as outpatient sewage, ward sewage, operating room sewage, blood bank sewage, laboratory sewage, inpatient ward sewage and the like based on graphene nano technologies, so as to ensure the safe discharge of various medical sewages and serve the construction of green medical institutions in various places.

Referring to FIG. 1, a schematic diagram of a multi-stage medical sewage sterilization device based on graphene nano technologies according to the present invention is shown. The multi-stage sterilization device includes a sewage discharge unit and a sterilization unit, and the sterilization unit is connected with the sewage discharge unit through a first-stage water valve 7. The medical sewage discharged from a medical institution unit 1 is collected by a power device such as a circulating water pump, a liquid ring vacuum pump, etc., as well as a special sewage settling tank and flows out into the sewage discharge unit after centralized settling.

The sewage discharge unit sequentially includes a first-stage graphene nano composite grid 2, a U-shaped graphene-reinforced polymer sewage discharge pipe 5, a second-stage graphene nano composite grid 3 and a third-stage graphene nano composite grid 4 along a water flow direction. Medical sewage enters the U-shaped graphene-reinforced polymer sewage discharge pipe 5 through the first-stage graphene nano composite grid 2 under power traction, and water coming out from the U-shaped graphene-reinforced polymer sewage discharge pipe 5 sequentially passes through the second-stage graphene nano composite grid 3 and the third-stage graphene nano composite grid 4.

The first-stage graphene nano composite grid has a mesh number of 50-120; the second-stage graphene nano composite grid has a mesh number of 120-250; and the third-stage graphene nano composite grid has a mesh number of 270-600. The three stages of graphene nano composite grids can be disassembled and cleaned regularly. The first two stages of graphene nano composite grids can filter and remove sand, rust, fine precipitates, flocculent floaters and the like in the medical sewage stage by stage, and the third-stage graphene nano composite grid can further block residual solid contaminants. The three stages of graphene nano composite grids are adjustable in mesh number according to the source and characteristics of the medical sewage, and based on the antibacterial property of the graphene, the three stages of graphene nano composite grids can not only block solid contaminants, but also play a preliminary sterilization effect on medical sewage to a certain extent.

The three stages of graphene nano composite grids are composed of graphene-reinforced polymer materials, wherein the polymer materials may be any one or more of polysulfone (PS), sulfonated polysulfone (SPS), polyethersulfone (PES), polypropylene (PP), polyacrylonitrile (PAN), polyvinylidene fluoride (PVDF), polytetrafluoroethylene (PTE), reinforced polypropylene (RPP), polycarbonate (PC), fluororubber, ethylene propylene rubber, nitrile rubber, chloroprene rubber, polyetheretherketone (PEEK), chlorinated polyvinyl chloride (CPVC). The graphene may be different graphene nanomaterials such as single-layer graphene, multi-layer graphene, single-layer graphene oxide, multi-layer graphene oxide, nitrogen-doped graphene, boron-doped graphene, organic or polymer-modified graphene, metal particle-modified graphene, and the like. The doping ratio of the graphene is 0.25-25%, preferably 2.5%.

The bottom of the U-shaped graphene-reinforced polymer sewage discharge pipe 5 is provided with a solid contaminant separation valve 6. After the medical sewage passes through the first-stage graphene nano composite grid 2, residual solid contaminants in the medical sewage slowly settles and is discharged through the solid contaminant separation valve 6. Solid contaminants that do not pass through the second-stage graphene nano composite grid 3 also settle down and are discharged through the solid contaminant separation valve 6.

The sterilization unit sequentially includes a graphene photocatalytic sterilization tank 8, a graphene-modified diatom ceramic disinfection tank 13, an ultrasonic sterilization tank 17 and a laser sterilization device along a water flow direction, and adjacent components are connected through a second-stage water valve 12, a third-stage water valve 16, and a fourth-stage water valve 18.

The medical sewage purified and preliminarily sterilized by the three stages of graphene nano composite grids enters the graphene photocatalytic sterilization tank 8 through the first-stage water valve 7. A wall of the graphene photocatalytic sterilization tank 8 is made of a transparent material, specifically glass, quartz, or a transparent polymer material, etc. An inner wall of the sterilization tank 8 is a graphene nano composite coating with photocatalytic effect, and the inside of the sterilization tank 8 is filled with graphene photocatalytic sterilization agent 10. As a further optimization, the inside of the graphene photocatalytic sterilization tank 8 is further provided with a stirring device 9 having a surface coated with a graphene photocatalytic coating, and the stirring device 9 is connected with the power control device 11 for stirring and agitation. The graphene nano composite coating may be any one or more of a titanium dioxide nanoparticle (or rod, tube, crystal, film)/graphene oxide (or graphene) composite material, phosphotungstic acid/graphene (or graphene oxide), tungsten trioxide/graphene (or graphene oxide), zinc oxide/graphene (or graphene oxide) and other nano composite materials. The graphene photocatalytic sterilization agent 10 may be any one or more of graphene oxide/titanium dioxide nanoparticles, graphene oxide/titanium dioxide nanobelts, graphene oxide/titanium dioxide nanotubes, graphene/titanium dioxide nanorods, phosphotungstic acid/graphene oxide, tungsten trioxide/graphene oxide, and zinc oxide/graphene oxide composite materials, and is continuously stirred and agitated by the stirring device 9 having the graphene photocatalytic coating coated on the surface, so as to kill pathogenic bacteria and residual parasite eggs in the medical sewage through a photocatalytic effect under light conditions, thereby achieving a photocatalytic sterilization effect.

The medical sewage after photocatalytic sterilization in the graphene photocatalytic sterilization tank 8 enters the graphene-modified diatom ceramic disinfection tank 13 through the second-stage water valve 12. Multiple layers of graphene-reinforced polymer screens 15 are distributed in the graphene-modified diatom ceramic disinfection tank 13, which are removable and washable and have a screen aperture of 100-600 mesh. The polymer material may be any one or more of PS, SPS, PES, PP, PAN, PVDF, PTE, RPP, PC, fluororubber, ethylene propylene rubber, nitrile rubber, chloroprene rubber, PEEK and CPVC. The graphene-modified diatom ceramic composite material 14 is regularly placed on the graphene-reinforced polymer screens 15, and the graphene-modified diatom ceramic composite material 14 is wrapped with a 100-325 mesh recycled fiber cloth or glass fiber cloth. Further, the graphene-modified diatom ceramic composite material 14 is formed by mixing a graphene oxide/superparamagnetic nanoparticle composite material and a graphene-reinforced diatom ceramic material in a mass ratio of 20:80 to 30:70. In the graphene oxide/superparamagnetic nanoparticle composite material, the graphene oxide accounts for 2.5-25%, preferably 2.5%. The material of the superparamagnetic nanoparticles may be any one or more of $\gamma$-$Fe_2O_3$, $Fe_3O_4$ and $Y_2O_3$, and the superparamagnetic nanoparticles have a particle size of less than 10 nm. Both the graphene oxide and the superparamagnetic material with a particle size of less than 10 nm have excellent antibacterial activity. After forming the composite material, a superimposed sterilization effect will be produced and possible pathogenic bacteria present in water such as *Escherichia coli, cholera* bacteria, *Shigella dysenteriae, salmonella, Klebsiella, schistosoma* pathogen, etc., can be better killed, thus achieving a further purification effect. The graphene-reinforced diatom ceramic material is prepared by sintering the following components in percentage by weight: 30-50% of diatomite, 10-30% of kaolin, 7-15% of feldspar, 2-15% of graphene, 2-4% of alumina, 2-4% of boron glass, 2-3% of talcum powder and 3-5% of quartz powder, and the weight percentage of graphene is preferably 2.5%. A composite of the graphene oxide/superparamagnetic nanoparticle composite material and the graphene-reinforced diatom ceramic material can form a certain "microchannel network" to effectively isolate or kill pathogenic bacteria with larger size.

The medical sewage disinfected by the graphene-modified diatom ceramic disinfection tank 13 enters the ultrasonic sterilization tank 17 through the third-stage water valve 16. Ultrasonic can assist in the sterilization with low energy consumption and short sterilization time. After the medical sewage enters the ultrasonic sterilization tank 17, the ultrasonic sterilization is performed at a power controlled within a range of 100 W to 500 KW for 10 to 60 min.

The medical sewage sterilized by the ultrasonic sterilization tank 17 enters the laser sterilization mechanism through the fourth-stage water valve 18. The fourth-stage water valve 18 may be provided with a residual solid contaminant separation port for separating residual solid contaminants. The laser sterilization mechanism includes a laser condensing cavity 20 and a laser generator 21, and a laser beam 22 generated by the laser generator 21 enters the laser condensing cavity 20. The laser condensing cavity 20 has a size ranging between 0.1 and 50 m, and may be formed entirely from aluminum, copper, stainless steel, high-strength heat-resistant ceramic or glass, etc., and an inner wall of the laser condensing cavity 20 is coated with graphene near-infrared nano coating 19. The graphene near-infrared nano coating 19 may be any one or more of a tin oxide nano-particle/graphene nano composite material, a titanium dioxide nanoband/graphene nano composite material, a titanium dioxide nano-particle/graphene nano material, a nitrogen-doped graphene nano material, a boron-doped graphene nano material, a graphene oxide/metal nano composite material, a liquid crystal/graphene oxide nano composite material, and a magnetic particle/graphene nano composite material. A thermal insulation layer is further provided below the graphene near-infrared nano coating 19, which may be any one or more of polyethylene terephthalate, parylene, polyarylether, polyimide, polybenzimidazole, polyquinoline, polypyrrole, graphite-type ladder polymer and phenanthroline ladder polymer. The laser generator 21 may be a neodymium glass laser, neodymium-doped yttrium aluminum garnet, a continuous wave tunable titanium sapphire laser or a near-infrared helium-neon laser, which is composed of a laser working substance, a pump source, a condensing cavity, a resonant cavity, a cooling system, etc., and operates in a continuous mode, a pulse mode, etc. The laser generator 21 further includes a power regulating valve, and near-infrared light with a wavelength range of 780-2526 nm can be obtained through regulation of the power regulating valve. Near-infrared light (NIR) is an electromagnetic wave between visible light (VIS) and mid-infrared light (MIR), which is defined as an electromagnetic wave with a wavelength in the range of 780 to 2526 nm by ASTM (American Society for Testing and Materials). Graphene-based nanomaterials can strongly absorb near-infrared light and can rapidly heat up in a short time, thus inducing apoptosis of a large number of residual contaminating bacterial cells in the medical sewage and necrosis of a small number of said bacterial cells.

The medical sewage entering the laser condensing cavity 20 is irradiated by the laser beam 22 for 5-60 min to be sterilized, and the graphene near-infrared nano coating 19 generates a strong near-infrared thermal effect at the same time of sterilization. Taking a titanium dioxide nanobelt/graphene nano material as an example, after absorbing near-infrared light having a wavelength of 1064 nm, the temperature of the titanium dioxide nanobelt/graphene nano material can rise from room temperature to 65° C. in 150 seconds, causing apoptosis of a large number of pathogenic bacteria or parasite eggs remaining in the laser condensing cavity 20 and necrosis of a small number of said pathogenic bacteria or parasite eggs, thus achieving the goal of sterilization or disinfection. As a further optimization, the bottom of the laser condensing cavity 20 is fixed on a rotatable sterilization tank base 23 which rotates at a speed of 5-60 rpm. A battery is arranged inside the rotatable sterilization tank base 23. A lower part of the sterilization tank is fixed by threads and the sterilization tank is detachable to be replaced by sterilization tanks with different diameters. Through rotation of the rotatable sterilization tank base 23, near-infrared light can be absorbed at all angles in the laser condensing cavity 20, and residual bacteria can be quickly killed by heating up. Combined with the sterilization effect of the laser beam itself, the sterilization of medical sewage can be more uniform and thorough.

After passing through the U-shaped graphene-reinforced polymer sewage discharge pipe, the three stages of graphene nano composite sterilization grids, the solid contaminant separation valve, the graphene photocatalytic sterilization tank, the graphene-modified diatom ceramic disinfection tank, the ultrasonic sterilization tank, the rotatable laser and near-infrared sterilization cavity and other different medical sewage discharge and sterilization units, the medical sewage is discharged through the fifth-stage water valve 24 to obtain a multi-stage sterilized water 25, and a sterilized water collection device and a deep purification device are subsequently connected.

Compared with the prior art, the device of the invention has a more thorough killing or blocking effect on pathogenic bacteria, parasite eggs and the like in various medical sewages, and the detection indexes of the medical sewage after the final sterilization treatment are as follows: three consecutive samples of 500 ml sewage are taken for detection after sterilization, and no pathogenic bacteria or parasite eggs shall be detected; the total number of coliform bacteria per liter shall not be more than 100 and shall conform to relevant national standards. In addition, the device of the present invention can be disassembled and cleaned regularly, and has a long service life, thus the process cost is reduced.

The present invention also provides a multi-stage medical sewage sterilization method based on graphene nano technologies, by which the medical sewage is sequentially passed through three stages of graphene nano composite grids with an increasing mesh number to obtain a preliminary sterilized water body; and then the preliminary sterilized water body is sequentially subjected to graphene photocatalytic sterilization, graphene-modified diatom ceramic composite sterilization, ultrasonic sterilization, laser and near-infrared sterilization to obtain a final sterilized water body.

The present invention is further illustrated by the following examples.

EXAMPLE 1

Medical sewage from hospital ward 1 is discharged through a U-shaped graphene-reinforced polymer sewage discharge pipe 5 after settling in a sewage settling tank, and passes sequentially through a first-stage graphene nano composite grid 2 (60 mesh), a second-stage graphene nano composite grid 3 (150 mesh), and a third-stage graphene nano composite grid 4 (300 mesh) to filter and remove sand, rust, fine precipitates, flocculent floaters and the like in the medical sewage stage by stage, to be preliminarily sterilized based on the antibacterial property of graphene or graphene oxide. The graphene nano composite grid is composed of graphene and PVDF, and the amount of graphene added is 2.5%. The residual solid contaminants that settle down slowly during this period are discharged through the solid contaminant separation valve 6 at the bottom of the U-shaped graphene-reinforced polymer sewage discharge pipe 5.

The medical sewage purified and preliminarily sterilized by the three stages of graphene nano composite grids enters the graphene photocatalytic sterilization tank 8 through a first-stage water valve 7. A wall of the graphene photocatalytic sterilization tank is made of transparent glass, and an inner wall of the graphene photocatalytic sterilization tank is a titanium dioxide nanobelt/graphene nano composite coating with photocatalytic effect. The medical sewage entering the graphene photocatalytic sterilization tank 8 is stirred and agitated by a stirring device 9 (connected with a power control device 11) coated with a titanium dioxide nanobelt/graphene nano composite coating on the surface, and a photocatalytic sterilization agent 10 of a titanium dioxide nano-particle/graphene nano composite material is added in batches. Pathogenic bacteria and residual parasite eggs in the medical sewage are killed through the photocatalytic effect under light conditions, thus achieving the bacteriostatic and sterilization effect.

The medical sewage after photocatalytic sterilization enters the graphene-modified diatom ceramic disinfection tank 13 through a second-stage water valve 12. Multiple layers of graphene/polysulfone nano composite screens 15 are distributed in the graphene-modified diatom ceramic disinfection tank 13, which are removable and washable and have a screen aperture of 200 mesh. A graphene-modified diatom ceramic composite material 14 is regularly placed on the graphene-reinforced polymer screens 15, which is formed by mixing a graphene/superparamagnetic nanoparticle composite material (A) and a graphene-reinforced diatom ceramic material (B) in a ratio of 30:70. In the graphene/superparamagnetic nanoparticle composite material, the superparamagnetic nanoparticles are $\gamma\text{-Fe}_2\text{O}_3$ with a particle size of 5 nm or less, and the ratio of the graphene added is preferably 2.5%. The graphene-reinforced diatom ceramic material is prepared by sintering the following components in percentage by weight: 45% of diatomite, 25.5% of kaolin, 12.5% of feldspar, 2.5% of graphene, 3.5% of alumina, 3.5% of boron glass, 2.5% of talcum powder and 5.0% of quartz powder. A composite of the graphene oxide/ superparamagnetic nanoparticle composite material and the graphene-reinforced diatom ceramic material is wrapped with a 200-mesh recycled fiber cloth.

The medical sewage disinfected by the graphene-modified diatom ceramic disinfection tank 13 enters the ultrasonic sterilization tank 17 through a third-stage water valve 16 and is ultrasonically sterilized at a power of 10 KW for 20 min.

After ultrasonic sterilization, the medical sewage enters a stainless steel laser condensing cavity 20 through a fourth-stage water valve 18 (provided with a residual solid contaminant separation port to separate the residual solid contaminants). The laser condensing cavity 20 has a size of 2.0 m, and an inner wall of the laser condensing cavity 20 is coated with a tin oxide nanoparticle/graphene composite material near-infrared nano coating 19. A polyarylether thermal insulation layer is arranged below the near-infrared nano coating. A pulsed Nd-glass laser 21 is selected and near-infrared light having a wavelength of 1026 nm can be obtained through regulation of a power regulating valve. After entering the laser condensing cavity 20, the treated medical sewage is irradiated by a laser beam 22 for 15 min to be sterilized. At the same time, the tin oxide nanoparticle/graphene composite material near-infrared nano coating 19 produces a strong near-infrared thermal effect, causing apoptosis of a large number of pathogenic bacteria or parasite eggs remaining in the laser condensing cavity 20 and necrosis of a small number of said pathogenic bacteria or parasite eggs, thereby achieving the goal of sterilization or disinfection. Further, the bottom of the laser condensing cavity 20 is fixed on a rotatable sterilization tank base 23 which rotates at a speed of 30 rpm. A battery is arranged inside the rotatable sterilization tank base 23. A lower part of the sterilization tank is fixed by threads and the sterilization tank is detachable to be replaced by sterilization tanks with different diameters. Through rotation of the rotatable sterilization tank base 23, near-infrared light can be absorbed at all angles in the laser condensing cavity 20, and residual bacteria can be quickly killed by heating up. Combined with the sterilization effect of the laser beam itself, the sterilization of medical sewage can be more uniform and thorough.

After passing sequentially through the U-shaped graphene-reinforced polymer sewage discharge pipe, the three stages of graphene nano composite sterilization grids, the solid contaminant separation valve, the graphene photocatalytic sterilization tank, the graphene-modified diatom ceramic disinfection tank, the ultrasonic sterilization tank, the rotatable laser and near-infrared sterilization cavity and other different medical sewage discharge and sterilization units, the medical sewage is discharged through a fifth-stage water valve 24 to obtain a multi-stage sterilized water 25, and a sterilized water collection device and a deep purification device are subsequently connected.

EXAMPLE 2

Medical sewage from hospital ward 1 is discharged through a U-shaped graphene-reinforced polymer sewage discharge pipe 5 after settling in a sewage settling tank, and passes sequentially through a first-stage graphene nano composite grid 2 (100 mesh), a second-stage graphene nano composite grid 3 (180 mesh), and a third-stage graphene nano composite grid 4 (350 mesh) to filter and remove sand, rust, fine precipitates, flocculent floaters and the like in the medical sewage stage by stage, to be preliminarily sterilized based on the antibacterial property of graphene or graphene oxide. The graphene nano composite grid is composed of graphene and PES, and the amount of graphene added is 2.5%. The residual solid contaminants that settle down slowly during this period are discharged through the solid contaminant separation valve 6 at the bottom of the U-shaped graphene-reinforced polymer sewage discharge pipe 5.

The medical sewage purified and preliminarily sterilized by the three stages of graphene nano composite grids enters the graphene photocatalytic sterilization tank 8 through a first-stage water valve 7. A wall of the graphene photocatalytic sterilization tank is made of transparent quartz, and an inner wall of the graphene photocatalytic sterilization tank is a tungsten trioxide/graphene oxide nano composite coating with photocatalytic effect. The medical sewage entering the graphene photocatalytic sterilization tank 8 is stirred and agitated by a stirring device 9 (connected with a power control device 11) coated with a tungsten trioxide/graphene oxide nano composite coating on the surface, and a photocatalytic sterilization agent 10 of a titanium dioxide nanoparticle/graphene nano composite material is added in batches. Pathogenic bacteria and residual parasite eggs in the medical sewage are killed through the photocatalytic effect under light conditions, thus achieving the bacteriostatic and sterilization effect.

The medical sewage after photocatalytic sterilization enters the graphene-modified diatom ceramic disinfection tank 13 through a second-stage water valve 12. Multiple layers of graphene/polytetrafluoroethylene composite material screens 15 are distributed in the graphene-modified diatom ceramic disinfection tank 13, which are removable and washable and have a screen aperture of 150 mesh. A graphene-modified diatom ceramic composite material 14 is regularly placed on the graphene/polytetrafluoroethylene nano composite material screens 15, which is formed by mixing a graphene/superparamagnetic nanoparticle composite material (A) and a graphene-reinforced diatom ceramic material (B) in a ratio of 25:75. In the graphene/superparamagnetic nanoparticle composite material, the superparamagnetic nanoparticles are $Fe_3O_4$ with a particle size of 10 nm or less, and the ratio of the graphene added is preferably 3%. The graphene-reinforced diatom ceramic material is prepared by sintering the following components in percentage by weight: 49% of diatomite, 19.5% of kaolin, 14% of feldspar, 3.0% of graphene, 3.5% of alumina, 3.5% of boron glass, 2.5% of talcum powder and 5.0% of quartz powder. A composite of the graphene oxide/superparamagnetic nanoparticle composite material and the graphene-reinforced diatom ceramic material is wrapped with a 150-mesh recycled fiber cloth.

The medical sewage disinfected by the graphene-modified diatom ceramic disinfection tank 13 enters the ultrasonic sterilization tank 17 through a third-stage water valve 16 and is ultrasonically sterilized at a power of 25 KW for 15 min.

After ultrasonic sterilization, the medical sewage enters a stainless steel laser condensing cavity 20 through a fourth-stage water valve 18 (provided with a residual solid contaminant separation port to separate the residual solid contaminants). The laser condensing cavity 20 has a size of 3.5 m, and an inner wall of the laser condensing cavity 20 is coated with a titanium dioxide nanoparticle/graphene nano material near-infrared nano coating 19. A polypyrrole thermal insulation layer is arranged below the near-infrared nano coating. A pulsed neodymium-doped yttrium-aluminum garnet laser 21 is selected and near-infrared light having a wavelength of 1026 nm can be obtained through regulation of a power regulating valve. After entering the laser condensing cavity 20, the treated medical sewage is irradiated by a laser beam 22 for 10 min to be sterilized. At the same time, the titanium dioxide nanoparticle/graphene nano material near-infrared nano coating 19 produces a strong near-infrared thermal effect, causing apoptosis of a large number of pathogenic bacteria or parasite eggs remaining in the laser condensing cavity 20 and necrosis of a small number of said pathogenic bacteria or parasite eggs, thereby achieving the goal of sterilization or disinfection. Further, the bottom of the laser condensing cavity 20 is fixed on a rotatable sterilization tank base 23 which rotates at a speed of 15 rpm. A battery is arranged inside the rotatable sterilization tank base 23. A lower part of the sterilization tank is fixed by threads and the sterilization tank is detachable to be replaced by sterilization tanks with different diameters. Through rotation of the rotatable sterilization tank base 23, near-infrared light can be absorbed at all angles in the laser condensing cavity 20, and residual bacteria can be quickly killed by heating up. Combined with the sterilization effect of the laser beam itself, the sterilization of medical sewage can be more uniform and thorough.

After passing sequentially through the U-shaped graphene-reinforced polymer sewage discharge pipe, the three stages of graphene nano composite sterilization grids, the solid contaminant separation valve, the graphene photocatalytic sterilization tank, the graphene-modified diatom ceramic disinfection tank, the ultrasonic sterilization tank, the rotatable laser and near-infrared sterilization cavity and other different medical sewage discharge and sterilization units, the medical sewage is discharged through a fifth-stage water valve 24 to obtain a multi-stage sterilized water 25, and a sterilized water collection device and a deep purification device are subsequently connected.

EXAMPLE 3

Medical sewage from hospital ward 1 is discharged through a U-shaped graphene-reinforced polymer sewage discharge pipe 5 after settling in a sewage settling tank, and passes sequentially through a first-stage graphene nano composite grid 2 (80 mesh), a second-stage graphene nano composite grid 3 (200 mesh), and a third-stage graphene nano composite grid 4 (500 mesh) to filter and remove sand, rust, fine precipitates, flocculent floaters and the like in the medical sewage stage by stage, to be preliminarily sterilized based on the antibacterial property of graphene or graphene oxide. The graphene nano composite grid is composed of graphene and polycarbonate (PC), and the amount of graphene added is 3.0%. The residual solid contaminants that settle down slowly during this period are discharged through the solid contaminant separation valve 6 at the bottom of the U-shaped graphene-reinforced polymer sewage discharge pipe 5.

The medical sewage purified and preliminarily sterilized by the three stages of graphene nano composite grids enters the graphene photocatalytic sterilization tank 8 through a first-stage water valve 7. A wall of the graphene photocatalytic sterilization tank is made of poly carbonate, and an inner wall of the graphene photocatalytic sterilization tank is a phosphotungstic acid/graphene oxide composite coating with photocatalytic effect. The medical sewage entering the graphene photocatalytic sterilization tank 8 is stirred and agitated by a stirring device 9 (connected with a power control device 11) coated with a phosphotungstic acid/graphene oxide composite coating on the surface, and a photocatalytic sterilization agent 10 of a titanium dioxide nanorod/graphene nano composite material is added in batches. Pathogenic bacteria and residual parasite eggs in the medical sewage are killed through the photocatalytic effect under light conditions, thus achieving the bacteriostatic and sterilization effect.

The medical sewage after photocatalytic sterilization enters the graphene-modified diatom ceramic disinfection tank 13 through a second-stage water valve 12. Multiple layers of graphene/polyetheretherketone nano composite material screens 15 are distributed in the graphene-modified diatom ceramic disinfection tank 13, which are removable and washable and have a screen aperture of 120 mesh. A graphene-modified diatom ceramic composite material 14 is regularly placed on the graphene/polyetheretherketone nano composite material screens 15, which is formed by mixing a graphene/superparamagnetic nanoparticle composite material (A) and a graphene-reinforced diatom ceramic material (B) in a ratio of 30:70. In the graphene/superparamagnetic nanoparticle composite material, the superparamagnetic nanoparticles are $Y_2O_3$ with a particle size of 10 nm or less, and the ratio of the graphene added is preferably 2.5%. The graphene-reinforced diatom ceramic material is prepared by sintering the following components in percentage by weight: 43.5% of diatomite, 26% of kaolin, 13% of feldspar, 2.5% of graphene, 3.5% of alumina, 3.5% of boron glass, 2.5% of talcum powder and 5.0% of quartz powder. A composite of the graphene oxide/superparamagnetic nanoparticle composite material and the graphene-reinforced diatom ceramic material is wrapped with a 300-mesh recycled fiber cloth.

The medical sewage disinfected by the graphene-modified diatom ceramic disinfection tank 13 enters the ultrasonic sterilization tank 17 through a third-stage water valve 16 and is ultrasonically sterilized at a power of 15 KW for 12 min.

After ultrasonic sterilization, the medical sewage enters a high-strength heat-resistant ceramic laser condensing cavity 20 through a fourth-stage water valve 18 (provided with a residual solid contaminant separation port to separate the residual solid contaminants). The laser condensing cavity 20 has a size of 1.6 m, and an inner wall of the laser condensing cavity 20 is coated with a copper sulphide/graphene composite material near-infrared nano coating 19. A polyarylether thermal insulation layer is arranged below the near-infrared nano coating. A continuous near-infrared He—Ne laser 21 is selected and near-infrared light having a wavelength of 980 nm can be obtained through regulation of a power regulating valve. After entering the laser condensing cavity 20, the treated medical sewage is irradiated by a laser beam 22 for 30 min to be sterilized. At the same time, the copper sulphide/graphene composite material near-infrared nano coating 19 produces a strong near-infrared thermal effect, causing apoptosis of a large number of pathogenic bacteria or parasite eggs remaining in the laser condensing cavity 20 and necrosis of a small number of said pathogenic bacteria or parasite eggs, thereby achieving the goal of sterilization or disinfection. Further, the bottom of the laser condensing cavity 20 is fixed on a rotatable sterilization tank base 23 which rotates at a speed of 20 rpm. A battery is arranged inside the rotatable sterilization tank base 23. A lower part of the sterilization tank is fixed by threads and the sterilization tank is detachable to be replaced by sterilization tanks with different diameters. Through rotation of the rotatable sterilization tank base 23, near-infrared light can be absorbed at all angles in the laser condensing cavity 20, and residual bacteria can be quickly killed by heating up. Combined with the sterilization effect of the laser beam itself, the sterilization of medical sewage can be more uniform and thorough.

After passing sequentially through the U-shaped graphene-reinforced polymer sewage discharge pipe, the three stages of graphene nano composite sterilization grids, the solid contaminant separation valve, the graphene photocatalytic sterilization tank, the graphene-modified diatom ceramic disinfection tank, the ultrasonic sterilization tank, the rotatable laser and near-infrared sterilization cavity and other different medical sewage discharge and sterilization units, the medical sewage is discharged through a fifth-stage water valve 24 to obtain a multi-stage sterilized water 25, and a sterilized water collection device and a deep purification device are subsequently connected.

The above examples illustrate only several embodiments of the present invention, and the description thereof is more specific and detailed, but it is not intended to be understood as limiting the scope of the invention patent. It should be noted modifications and improvements may be made by those ordinary skilled in the art without departing from the concept of the present invention, all of which fall within the scope of the present invention.

What is claimed is:

1. A multi-stage medical sewage sterilization device based on graphene nano technologies, characterized by comprising:
   a sewage discharge unit including sequentially a first-stage graphene nano composite grid, a second-stage graphene nano composite grid and a third-stage graphene nano composite grid along a water flow direction, wherein mesh numbers of the first, second and third-stage graphene nano composite grids are sequentially increased;
   a sterilization unit connected with the sewage discharge unit through a first-stage water valve, and medical sewage sequentially passes through the three stages of graphene nano composite grids and enters the sterilization unit; the sterilization unit sequentially includes a graphene photocatalytic sterilization tank, a graphene-modified diatom ceramic disinfection tank, an ultrasonic sterilization tank and a laser sterilization device along a water flow direction, and adjacent components are connected through a second-stage water valve, a third-stage water valve and a fourth-stage water valve; a wall of the graphene photocatalytic sterilization tank is made of transparent material, an inner wall of the graphene photocatalytic sterilization tank is provided with a graphene nano composite coating, and the interior of the graphene photocatalytic sterilization tank is filled with graphene photocatalytic sterilization agent; the graphene-modified diatom ceramic disinfection tank is internally provided with multiple layers of graphene-reinforced polymer screens each having a graphene-modified diatom ceramic composite material provided thereon; and the laser sterilization device includes a laser condensing cavity and a laser generator, a laser beam generated by the laser generator enters the laser condensing cavity, and a graphene near-infrared nano coating is provided on an inner wall of the laser condensing cavity.

2. The multi-stage medical sewage sterilization device based on graphene nano technologies according to claim 1, characterized in that the first-stage graphene nano composite grid has a mesh number of 50-120; the second-stage graphene nano composite grid has a mesh number of 120-250; and the third-stage graphene nano composite grid has a mesh number of 270-600.

3. The multi-stage medical sewage sterilization device based on graphene nano technologies according to claim 2, characterized in that a U-shaped graphene-reinforced polymer sewage discharge pipe is arranged between the first-stage graphene nano composite grid and the second-stage graphene nano composite grid, and a solid contaminant separation valve is provided at the bottom of the U-shaped graphene-reinforced polymer sewage discharge pipe.

4. The multi-stage medical sewage sterilization device based on graphene nano technologies according to claim 3, characterized in that the graphene-modified diatom ceramic composite material is wrapped with a 100-325 mesh recycled fiber cloth or glass fiber cloth.

5. The multi-stage medical sewage sterilization device based on graphene nano technologies according to claim 4, characterized in that the graphene-modified diatom ceramic composite material is formed by mixing a graphene oxide/superparamagnetic nanoparticle composite material and a graphene-reinforced diatom ceramic material in a mass ratio of 20:80 to 30:70.

6. The multi-stage medical sewage sterilization device based on graphene nano technologies according to claim 5, characterized in that in the graphene oxide/superparamagnetic nanoparticle composite material, the graphene oxide accounts for 2.5-25%, and the superparamagnetic nanoparticles have a particle size of less than 10 nm.

7. The multi-stage medical sewage sterilization device based on graphene nano technologies according to claim 6, characterized in that the graphene-reinforced diatom ceramic material is prepared by sintering the following components in percentage by weight: 30-50% of diatomite, 10-30% of kaolin, 7-15% of feldspar, 2-15% of graphene, 2-4% of alumina, 2-4% of boron glass, 2-3% of talcum powder and 3-5% of quartz powder.

8. The multi-stage medical sewage sterilization device based on graphene nano technologies according to claim 7, characterized in that the ultrasonic power in the ultrasonic sterilization tank is 100 W to 500 KW, and the sterilization is performed for 10 to 60 min.

9. The multi-stage medical sewage sterilization device based on graphene nano technologies according to claim 8, characterized in that the bottom of the laser condensing cavity is fixed on a rotatable sterilization tank base which rotates at a speed of 5-60 rpm.

10. A multi-stage medical sewage sterilization method based on graphene nano technologies, characterized in that the medical sewage is sequentially passed through three stages of graphene nano composite grids with an increasing mesh number to obtain a preliminary sterilized water body; and then the preliminary sterilized water body is sequentially subjected to graphene photocatalytic sterilization, graphene-modified diatom ceramic composite sterilization, ultrasonic sterilization, laser and near-infrared sterilization to obtain a final sterilized water body.

* * * * *